US012245837B2

(12) United States Patent
Simi et al.

(10) Patent No.: US 12,245,837 B2
(45) Date of Patent: Mar. 11, 2025

(54) STERILE MASTER INPUT HANDLE ASSEMBLY FOR A ROBOTIC SURGERY SYSTEM AND SURGICAL DRAPE FOR A STERILE MASTER INPUT HANDLE

(71) Applicant: MEDICAL MICROINSTRUMENTS, INC., Pisa (IT)

(72) Inventors: Massimiliano Simi, Pisa (IT); Federico Montagnani, Pisa (IT)

(73) Assignee: Medical Microinstruments, Inc., Wilmington, DE (US)

( * ) Notice: Subject to any disclaimer, the term of this patent is extended or adjusted under 35 U.S.C. 154(b) by 334 days.

(21) Appl. No.: 17/929,012

(22) PCT Filed: Feb. 9, 2021

(86) PCT No.: PCT/IB2021/051023
§ 371 (c)(1),
(2) Date: Aug. 10, 2022

(87) PCT Pub. No.: WO2021/161158
PCT Pub. Date: Aug. 19, 2021

(65) Prior Publication Data
US 2023/0114346 A1    Apr. 13, 2023

(30) Foreign Application Priority Data
Feb. 10, 2020    (IT) .................. 102020000002539

(51) Int. Cl.
*A61B 46/10*    (2016.01)
*A61B 34/00*    (2016.01)
(Continued)

(52) U.S. Cl.
CPC .............. *A61B 46/10* (2016.02); *A61B 34/20* (2016.02); *A61B 34/37* (2016.02); *A61B 34/74* (2016.02)

(58) Field of Classification Search
CPC ......... A61B 46/10; A61B 34/20; A61B 34/37; A61B 34/74; A61B 2034/2051; A61B 2034/2055
See application file for complete search history.

(56) References Cited

U.S. PATENT DOCUMENTS 8,368,649 B2    2/2013    Hall et al.
10,512,515 B2    12/2019    Bailey
(Continued)

FOREIGN PATENT DOCUMENTS

EP    2845556 A1    11/2015
EP    2467082 B1    4/2016
(Continued)

OTHER PUBLICATIONS

International Search Report and Written Opinion for International Patent Application No. PCT/IB2021/051023, mailed Apr. 21, 2021, 13 pp.

*Primary Examiner* — Tarla R Patel
(74) *Attorney, Agent, or Firm* — Armstrong Teasdale LLP (57) ABSTRACT

A sterile master input handle assembly includes a non-sterile manipulandum; a sterile surgical drape draping the non-sterile manipulandum; and at least one sterile accessory, suitable to form a sterile interface of the sterile master input handle assembly for the surgeon's fingers. The at least one sterile accessory mechanically engages with the non-sterile manipulandum across the sterile surgical drape, the at least one sterile accessory covers at least one portion of the outer surface of the surgical drape, and the at least one sterile accessory includes at least one surface forming the sterile interface for the surgeon's fingers to manipulate the non-sterile manipulandum across the sterile surgical drape.

14 Claims, 7 Drawing Sheets

(51) Int. Cl.
*A61B 34/20* (2016.01)
*A61B 34/37* (2016.01)

(56) References Cited

U.S. PATENT DOCUMENTS

| | | | |
|---|---|---|---|
| 2014/0018960 | A1 | 1/2014 | Itkowitz |
| 2019/0069969 | A1 | 3/2019 | Higuchi et al. |
| 2019/0192236 | A1* | 6/2019 | Shelton, IV .......... A61F 5/0036 |
| 2019/0328473 | A1* | 10/2019 | Chassot ............. A61B 18/1442 |

FOREIGN PATENT DOCUMENTS

| | | |
|---|---|---|
| JP | 6367019 B2 | 8/2018 |
| WO | 2014151621 A1 | 9/2014 |
| WO | 2017064301 A1 | 4/2017 |
| WO | 2018189729 A1 | 10/2018 |
| WO | 2019099584 A1 | 5/2019 |
| WO | 2019220407 A1 | 11/2019 |
| WO | 2019220408 A1 | 11/2019 |
| WO | 2019220409 A1 | 11/2019 |

* cited by examiner

STERILE MASTER INPUT HANDLE ASSEMBLY FOR A ROBOTIC SURGERY SYSTEM AND SURGICAL DRAPE FOR A STERILE MASTER INPUT HANDLE

CROSS-REFERENCE TO RELATED APPLICATIONS

This application is a National Stage Application of International Patent Application No. PCT/IB2021/051023, having an International Filing Date of Feb. 9, 2021, which claims priority to Italian Application No. 102020000002539, filed Feb. 10, 2020, each of which is hereby incorporated by reference in its entirety.

DESCRIPTION

Field of the Invention

It is an object of the present invention a sterile master input handle assembly.

The sterile master input handle assembly is suitable for robotic surgery.

The present invention also relates to a master controller assembly comprising at least one sterile master input handle assembly and a master console.

The present invention also relates to a robotic surgery system comprising at least one sterile master input handle assembly.

Furthermore, this disclosure relates to a surgical drape for a sterile master input handle.

Background Art

Robotic surgery apparatuses are used in robotic-aided surgery and generally comprise a surgeon master console for receiving a manual command from the surgeon, a robotic slave central tower (or robotic cart) and a plurality of robotic slave arms carrying one or more surgical instruments (end-effectors) extending from the slave central tower and controlled by means of said surgeon master console. Said one or more slave surgical instruments are distally attached to the robotic slave arms, in order to perform surgical procedures to a patient who lies within a sterile operatory field. Surgical drape draping non-disposable parts of the robotic apparatus is typically provided to avoid contamination of the sterile operatory field that may be caused by the robotic surgery apparatus. Straps and strings may be provided on the outer surface of the surgical drape for the purpose of tying the drape around the robot reducing the volume of the drape so that it results substantially tight fit.

For example, documents WO-2017-064301 and WO-2018-189729 in the name of the same Applicant disclose solutions of robotic surgery system, suitable for miniaturize the surgical instrument resulting suitable, inter alia, for robot-aided microsurgery. Traditional (non-robotic) microsurgery requires the surgeon to operate together with an operating microscope, typically an optical microscope, able to magnify the surgery field and therefore robotic surgery apparatuses for microsurgery are suitably equipped with an operating microscope. Surgical drapes for draping the microscope have been provided for, as shown for example in documents US-2019-0069969 and JP-6367019.

Microsurgery procedures are carried out in several phases of the reconstruction of biological tissues, such as for example in the execution of blood vessel anastomosis, comprising small diameter vessels and nerves, as well as in the reconstruction of anatomic parts after the occurrence of traumatic lesions, in re-vascularization of tissues, reattachment of limbs, in transplantation and replantation procedures. In the field of microsurgery, robotic apparatuses allow a high degree of miniaturization of the surgical instrument when compared to traditional microsurgery and allows at the same time to reduce the transmission of tremor to the slave surgical instrument of the robotic surgery system.

Robotic surgery apparatuses are also suitable for robot-aided laparoscopic surgery, where the surgical instruments and at least one camera are individually inserted inside the patient's body by means of a set of percutaneous trocars, and wherein a visualization screen visualizes the laparoscopic images of the inner patient's body acquired from the camera. Thanks to the robotic aid, it is reduced the fulcrum effect during surgery due to the lever arm formed across the length of each percutaneous rigid trocar during manipulation of traditional (non-robotic) laparoscopic surgical instruments. Moreover, thanks to the robotic aid, the laparoscopic surgeon is provided with an improved comfort during surgery due to the ergonomic features of the surgeon master console.

Remote surgeon master console have been provided for, as shown for example in documents US-2014-0018960 and EP-2845556. Generally, such remote surgeon master consoles comprise a visualization device, a surgeon seat and/or a surgeon forearm resting elements, and master control handles in form of appendices hinged to the body of the master console to receive a manual command from the surgeon for controlling the slave surgical instrument. Thereby, the comfort of the laparoscopic surgeon is even enhanced in that he/she is not required to even attend the sterile field of the operatory room and can perform surgery from a non-sterile remote location.

However, to have a wide physical distance between the team in the sterile operatory field and the surgeon handling the master input appendices at the remote master console may create communication problems during surgery among the team and in particular with the surgeon.

It is therefore felt the need for the surgeon to attend the sterile operatory field, even in presence of a robotic surgery system.

Moreover, in some applications of the robotic-aided microsurgery it is desirable the presence of the surgeon within the sterile operatory field during the robotic-aided surgery. Thereby, during a single intervention, the micro-surgeon can switch from robotic-aided microsurgery to traditional (non-robotic) microsurgery grabbing in hand traditional microsurgery tools, such as tweezers, and/or back to the surgeon master console.

For example, document US-2019-328473 shows a master console that may be covered with a sterile drape during operation attached to a sterile, exposed, constrained, motorized, master input appendices, which is rotatably mounted to the master console.

For example, document US-10512515 shows a non-sterile master input handle having and hand track ball and an integrated display which may be covered by a sterile drape. Document US-8368649 shows a similar solution, wherein a sterile mouse pad os positioned over an active sensing base to drive a computerized medical device.

For example, document WO-2014-151621 discloses a system for alternating hand surgery and robotic surgery using a mechanically ungrounded master controller that is designed for being hand held by the surgeon. Wearable and mechanically ungrounded master controllers are also known for example from documents WO-2019-099854 and EP-2467082, and typically comprise a pair of rings to fit the surgeon fingers integrally associated to a grip command interface of the ungrounded master controller.

Furthermore, documents WO-2019-220407, WO-2019-220408 and WO-2019-220409 in the name of the same Applicant disclose several embodiment of hand-held master input handles which are mechanically ungrounded and mechanically unconstrained with respect to the master console, so that they are freely movable with respect to the console within a predefined tracking volume, in order to control paired slave surgical instruments, and comprise a master gripper comprising an internal degree of freedom to control a paired grip degree of freedom of a paired slave surgical instrument, such as for example a needle holder slave surgical system. Mechanically unconstrained master input handles of the type mentioned above have recently been recently emerged as an advantageous solution for controlling a slave robotic surgery instrument in that they allow an increased range of motion for the surgeon, and a scale factor may be provided so that large movements of the surgeon translate into small movements of the slave robotic surgery instrument. Tracking devices, such as optical or magnetic, may be provided integrally to the master console to track the position and/or orientation of the mechanically unconstrained master input handles within a workspace. To this end, the master input handle may be equipped with optical markers and/or magnetometers.

However, unconstrained master input handles may need proper sterilization after/before use in a sterile environment, and it may result costly. Alternatively, unconstrained master input handles may be designed for a single use only, despite their high technological content and/or strict fabrication tolerances with the purpose of be tracked in their workspace with the highest level of spatial precision, and it may also result costly.

The need is felt to balance the conflicting needs of providing master input handles for robotic surgery able to accurately control paired slave surgical instruments while ensuring a high range of motion to the surgeon's hands and the same time without requiring to be single use, or at least limiting to the minimum the technological content, and therefore the costs of manufacturing and the material employed, of those parts of the master input handles needing to be disposable.

It is also felt the need of a solution that allow the surgeon to effectively alternate robot-aided surgery and traditional hand surgery.

At the same time, it is felt the need to simplify the switching from robot-aided surgery to traditional surgery in a single intervention, and vice-versa.

Solution

It is a scope of the present invention to overcome the drawbacks mentioned with reference to the known art and providing a solution of a master input handle for use in a sterile field.

It is a scope of the present invention to overcome the drawbacks mentioned with reference to the known art and providing a solution for draping a master input handle for use in a sterile field These and other scopes are achieved by a master input handle assembly, a master controller assembly, a roboti surgery system, and a surgical drape according to the present disclosure.

According to an aspect of the invention, a sterile master input handle assembly comprises a non-sterile manipulandum, a sterile surgical drape draping said non-sterile manipulandum and at least one sterile accessory suitable to form a sterile interface of the sterile master input handle assembly for the surgeon's fingers.

According to an aspect of the invention, said at least one sterile accessory mechanically engages with said non-sterile manipulandum across said sterile surgical drape, and said at least one sterile accessory covers at least one portion of the outer surface of the surgical drape, and said at least one sterile accessory includes at least one interface surface forming said sterile interface for the surgeon's fingers to manipulate the non-sterile manipulandum across said sterile surgical drape.

The sterile master input handle assembly may be designed to be hand-held by the surgeon during surgery. The surgeon may support entirely the weight of the hand-held sterile master input handle assembly during surgery.

The sterile master input handle assembly may be mechanically ungrounded and comprising features designed to be tracked by an associable tracking system to determine position and/or orientation of the master input handle assembly within a predefined work volume for controlling at least one paired slave surgical instrument. The work volume is preferably integral with a portion of the tracking system. The features designed to be tracked by an associable tracking system may comprise one or more optical markers and/or one or more magnetometers. The tracking system may be an optical tracking system comprising a camera set and/or may be a magnetic tracking system comprising a magnetic field generator. The sterile master input handle assembly is preferably freely movable with respect to the tracking system. The sterile master input handle assembly is preferably designed to be freely rolled between the surgeon's fingers.

Two sterile master input handle assemblies may be provided, one for each surgeon's hand.

The interface surface of the sterile accessory may be friction surface having a predefined value of surface roughness greater than the surface roughness of the outer surface of the surgical drape to improve the surgeon's grip over the sterile master input handle assembly during surgery.

The interface surface of the sterile accessory may be a convex surface, for facing one or more of the surgeon's finger. Such a convex interface surface may allow the surgeon to roll the sterile master input handle assembly with ease while the sterile master input handle assembly is held in a surgeon's hand.

The sterile master input handle assembly may include a further, second sterile accessory, so as to comprise at least two sterile accessories on a single master input handle assembly, in other words to have two sterile accessories engaged with a single non-sterile manipulandum across the surgical drape, thereby providing at least two opposite interface surfaces for the surgeon's fingers of a surgeon hand to grasp said non-sterile manipulandum across said sterile surgical drape. Preferably, a sterile master input handle assembly is designed to be hand-held by a single hand of the surgeon during surgery. Said two sterile accessories may be provided at opposite sides of the non-sterile manipulandum. Two sterile accessories may be provided opposite with respect to the body of said non-sterile manipulandum with the purpose to expose two convex interface surfaces in opposite direction, so that the two convex interface surfaces face away one in respect to the other.

The sterile master input handle assembly may comprise at least one degree of freedom between said two opposite interface surfaces. The at least one degree of freedom may be a grip degree of freedom designed to control a paired slave degree of freedom of grip of a slave surgical instrument. To actuate the grip degree of freedom, the two opposite interface surfaces may be moved, for example moved by means of application of a pressing action, towards each other by the surgeon's fingers. Said degree of freedom between the two opposite interface surfaces may be defined by the non-sterile manipulandum, which for example comprises two parts movable one in respect to the other, such as two articulated parts and/or a press-button and/or two parts slidingly associated to each other. Said degree of freedom between the two opposite interface surfaces may be defined by the at least one accessory itself, for example by means of a deformable bridge between two interface surfaces.

Said degree of freedom between the two opposite interface surfaces may be an elastically loaded degree of freedom. For example, the deformable bridge between two accessories is an elastically deformable bridge, which for example comprises or is made of a flat spring.

In at least one configuration, the elastic action of said elasically-loaded degree of freedom biases said two opposite interface surfaces away to each other.

In at least one configuration said two opposite interface surfaces define together a convex, cylindrical geometry. For example, when the sterile master input handle assembly is in a closed configuration, the closed configuration might be obtained by moving towards each other two articulated parts of the non-sterile manipulandum and/or the two opposite interface surfaces, then the two opposite interface surfaces define together a convex, cylindrical geometry. The provision of such a convex, cylindrical geometry favors the rolling of the sterile master input handle assembly between/among the surgeon's fingers of a surgeon's hand. Said two opposite sterile accessories may be made in single piece, in other words said two sterile accessories may be monobloc.

The non-sterile manipulandum may comprise at least a pair of elongated elements hinged one another forming a tool joint wherein at least one of the elongated elements comprises at least one convex body; and wherein said at least one sterile accessory is engaged with the convex body. Each of said elongated elements may comprise said convex body and said sterile accessory may be engaged with the convex body of each of said elongated elements.

The at least one interface surface may comprise bosses and/or valleys to receive the surgeon's fingers.

According to an aspect of the invention, a master controller assembly comprises at least one sterile master input handle assembly and at least one tracking system designed to track position and/or orientation of at least one portion of the at least one sterile master input handle assembly. The tracking system may belong to a master console of the master controller assembly in order to track position and/or orientation of the sterile master input handle assembly with respect to the master console. The master console may comprise a pair of sterile master input handle assemblies.

According to an aspect of the invention, a robotic surgery system comprises at least one sterile master input handle assembly and at least one slave robot assembly comprising at least one surgical instrument. The surgical instrument may comprise a grip degree of freedom controlled by the master input handle assembly.

According to an aspect of the invention, a robotic surgery system comprises a master controller assembly and at least one slave robot assembly comprising at least one surgical instrument. The surgical instrument may comprise a grip degree of freedom controlled by the master input handle assembly.

According to an aspect of the invention, a surgical drape for a master input handle assembly comprises a pair of pouches for respectively, i.e. individually, receiving a pair of elongated elements of a non-sterile manipulandum. The surgical drape may comprise a bifurcation from which said pair of pouches extend distally. Said pair of pouches may extend proximally from the bifurcation.

Thanks to the proposed solutions, a per se non-sterile manipulandum designed to receive a manual command from a user (i.e. a surgeon) in a sterile operatory field and can be reused for several surgeries.

Thanks to the proposed solutions, it is provided a master input handle assembly having a drape that drapes a master manipulandum, the assembly having a sterile accessory that may be coupled to the manipulandum in order to form an interface for the surgeon's fingers within a sterile operatory field. Furthermore, a manipulandum draped by a sterile barrier assembly exposes interface surfaces with the purpose of providing a stable grip of the surgeon's finger thereon during robotic-aided microsurgery.

The safety in the manipulation of the master controller for robotic surgery is enhanced because it is reduced the risk that the manipulandum draped by the surgical drape may slip between surgeon's fingers, which in absence of such a sterile accessory would expose the drape outer surface to the surgeon's fingers.

The proposed solutions are particularly suitable for, although not exclusively limited to, robotic-aided microsurgery. Furthermore, the proposed solutions are particularly suitable for, although not exclusively limited to, microsurgical procedures that contemplates the alternation of hand microsurgery and robot-aided microsurgery.

FIGURES

Further features and advantages of the assembly and the system according to the invention will become apparent from the following description of its preferred examples of embodiment, given by way of indicative and non-limiting example, with reference to the accompanying drawings wherein.

DETAILED DESCRIPTION OF SOME EMBODIMENTS

According to a general embodiment, a sterile master input handle assembly 302 for a robotic surgery system 300 comprises a non-sterile manipulandum 310 and a sterile surgical drape 303 draping said non-sterile manipulandum 310.

According to a preferred embodiment, said non-sterile manipulandum 310 is a non-sterile master controller 310 for a master-slave robotic surgery system 300.

According to a preferred embodiment, said non-sterile manipulandum 310 is per se unsuitable to be re-used within a sterile environment, such as a sterile operatory field 311.

According to a preferred embodiment, said non-sterile manipulandum 310 has body suitable for being hand-held by a surgeon.

Not necessarily said non-sterile manipulandum 310 is mechanically ungrounded from a master console 350 of the robotic surgery system 300, although according to a preferred embodiment said non-sterile manipulandum 310 is mechanically ungrounded.

According to a preferred embodiment the non-sterile manipulandum 310 is mechanically ungrounded, mechanically unconstrained from the robotic surgery system 300 and the non-sterile manipulandum 310 is designed to cooperate with a tracking system 339 of the robotic surgery system 300, such as an optical and/or magnetic tracking system, so that the position and/or orientation of the non-sterile manipulandum within a predefined work volume 320 can be tracked by the tracking system 339 for controlling a paired slave surgical instrument.

The sterile drape 303 may be a loose or close-fit sheet of surgical drape material, or it may be partly loose and partly close-fit, and is for example made of polymer material. For example, the body of the surgical drape 303 is made of flexible sheet, such as polyethylene, and/or polyurethane, and/or polyester.

According to an embodiment, said sterile drape 303 comprising body having an inner surface 304, or non-sterile surface 304, and an outer surface 305, or sterile surface 305, opposite to said inner non-sterile surface 304. Thereby, the outer surface 305 of the surgical drape 303 is designed to face the surgeon, and the inner surface 304 of the sterile drape 303 is designed to face said non-sterile manipulandum 310. According to a preferred embodiment, the body of the surgical drape 303 forms a drape cavity 322 for enclosing at least a portion of said non-sterile manipulandum 310 with the purpose of preserve sterility of the manipulandum 310. Thereby, the inner surface 304 of the drape 303 faces the cavity 322. The drape cavity 322 may be tight sealed or opened forming an opening 331 to access the cavity 322 that leads to said outer surface 305 of the surgical drape 303 from the cavity 322.

Said sterile master input handle assembly 302 comprises at least one sterile accessory 306, suitable to form a sterile interface of the sterile master input handle assembly 302 for the surgeon fingers. According to an embodiment, said at least one sterile accessory 306 forms a sterile handgrip of said sterile master input handle assembly 302.

Said at least one sterile accessory 306 mechanically engages with said non-sterile manipulandum 310 across said sterile surgical drape 303. Preferably, said mechanic engagement does not tear the sterile drape 303, in other words said the at least one sterile accessory 306 mechanically engages with said non-sterile manipulandum 310 across said sterile drape 303 while preserving the integrity of the sterile drape 303.

According to a preferred embodiment, said at least one sterile accessory 306 is made as a single piece, for example of molded polymer material that is harder and/or stiffer than the sterile drape 303. For example, the accessory 306 is made of a rigid shell, for example a molded polymeric rigid shell, for example made of polyethylene, and/or polyurethane, and/or polyester.

According to a preferred embodiment, a connector 308 is provided on said accessory 306 in order to mechanically engage with said non-sterile manipulandum 310 across said sterile drape 303. Said connector 308 may be integral with said accessory 306 and may snap-fit said non-sterile manipulandum 310.

Advantageously, said at least one sterile accessory 306 covers at least one portion of the outer surface 305 of the surgical drape 303. Thereby, at least one portion of the sterile drape 303 results interposed between said at least one accessory 306 and at least one portion of said non-sterile manipulandum 310.

With additional advantage, said at least one sterile accessory 306 includes at least one interface surface 307 forming said sterile interface for the surgeon fingers to manipulate the non-sterile manipulandum 310 across said sterile surgical drape 306.

Thanks to such a sterile accessory 306 it is possible to make the non-sterile manipulandum 310, which is draped, easier to handle for a surgeon, for example by a single hand of the surgeon.

At the same time, it is allowed to re-use the same non-sterile manipulandum 310 by means of sterilizing the accessory 306 and/or by means of providing a new sterile accessory 306 for a new surgery and/or a new step of the same surgery. Preferably, said accessory 306 can be sterilized with sterilization means for sterile operatory room, such as for example autoclave.

According to an embodiment, said at least one interface surface 307 is suitable for facing the surgeon and for forming said sterile interface for the surgeon fingers to manipulate the non-sterile manipulandum310 across said sterile surgical drape 306, when in use.

The sterile master input handle assembly 302 is designed to receive a manual command for actuating a robotic slave assembly 330, suitable for performing surgery, preferably microsurgery, to a patient's anatomy, of a master-slave teleoperated robotic microsurgery system 300. According to an embodiment, said at least one sterile accessory 306 covers at least one portion of the outer surface 305 of the surgical drape 303 that in turn covers at least one portion of said non-sterile manipulandum 310 that has or forms a grip controller designed for controlling a paired slave grip degree of freedom of a robotically actuated slave surgical instrument 337 operatively connected to said sterile master input handle 302. Thereby, the surgeon by means of acting, for example pressing or pushing, on said interface surface 307 of the accessory 306 is able to control a paired slave grip degree of freedom of a robotically actuated slave surgical instrument 337 operatively connected to said sterile master input handle 302.

According to an embodiment, said interface surface 307 of the sterile accessory 306 is a friction surface, for example a friction surface having a predefined value of surface roughness above a certain threshold greater than the surface roughness of the outer surface of the surgical drape 303. According to an embodiment, said interface surface 307 of the sterile accessory 306 defines one or more bosses 354 and/or recesses 354', such as bumps 354 and/or valleys 354', to facilitate the surgeon hold. According to an embodiment, said interface surface 307 of the sterile accessory 306 defines one or more cuts 327 or notches 327 to facilitate the surgeon hold and grip thereon. According to an embodiment, said interface surface 307 of the sterile accessory 306 is wrinkled or corrugated to facilitate the surgeon hold and grip thereon. According to an embodiment, said sterile accessory 306 comprises cuts 327 or notches 327 or incisions 327 that locally interrupt the continuity of the interface surface 307. Thereby, the friction of the interface surface 307 is further enhanced. For example, said cuts 327 or notches 327 extend transversally to the longitudinal extension of said sterile accessory 306. According to an embodiment, the interface surface 307 is molded so that to present coarse surface finish. According to an embodiment, the interface surface 307 is treated to increase friction thereof. For example, the surface roughness of the functional surface 307 may be enhanced by means of surface treatment of the sterile accessory 306.

According to an embodiment, said at least one sterile accessory 306 and said sterile surgical drape 303 are detachably associated one another. According to an embodiment, said at least one sterile accessory 306 and said sterile surgical drape 303 are made of different materials. According to an embodiment, said at least one sterile accessory 306 and said sterile surgical drape 303 result locally associated one another, preferably in a detachable manner, due to the fact that at least one portion of the sterile drape 303 is interposed between a portion of the non-sterile manipulandum 310 and said at least one accessory 306 when the accessory 306 and the non-sterile manipulandum 310 are mechanically engaged. In other words, preferably the accessory 306 does not attach to the outer surface 305 of the sterile drape 303 and the sterile drape is locally held against at least one portion of said non-sterile manipulandum by means of a retaining action exerted by the mechanical engagement of the sterile accessory 306 to the manipulandum 310 across at least one portion of the sterile drape 303. Thereby, there is no need to provide attachment means for attaching the at least one sterile accessory to said sterile drape 303 that may cause localized stress on the sterile drape 303, therefore the sterile drape 303 may be made thinner and of constant thickness, without for these reasons resulting too fragile when in use. The connector 308 of the sterile accessory 306 may act as local retaining element for at least one portion of the surgical drape 303 against the manipulandum 310. Thanks to the fact that the sterile accessory 306 is not attached to the sterile drape 303 but is engaged to the manipulandum 310 across the sterile drape's 303 thickness it is possible to lock in a predefined relative position and spatial orientation the interface surface 307 and active parts of the manipulandum 310.

Figure 11:
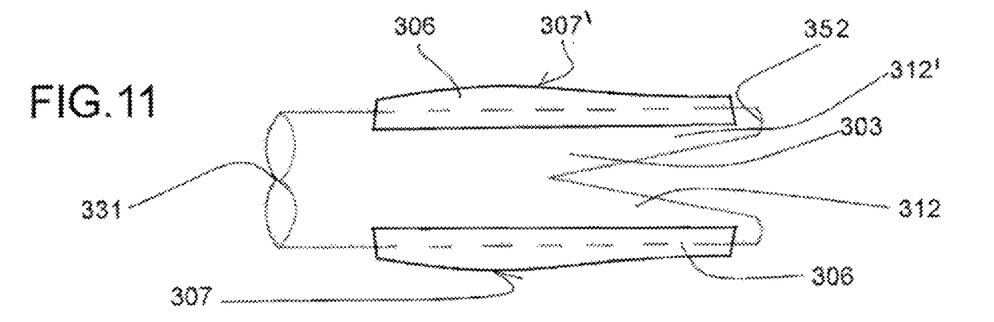
FIG. 11 shows a surgical drape integral with two accessories, according to an embodiment.
Figure 12:
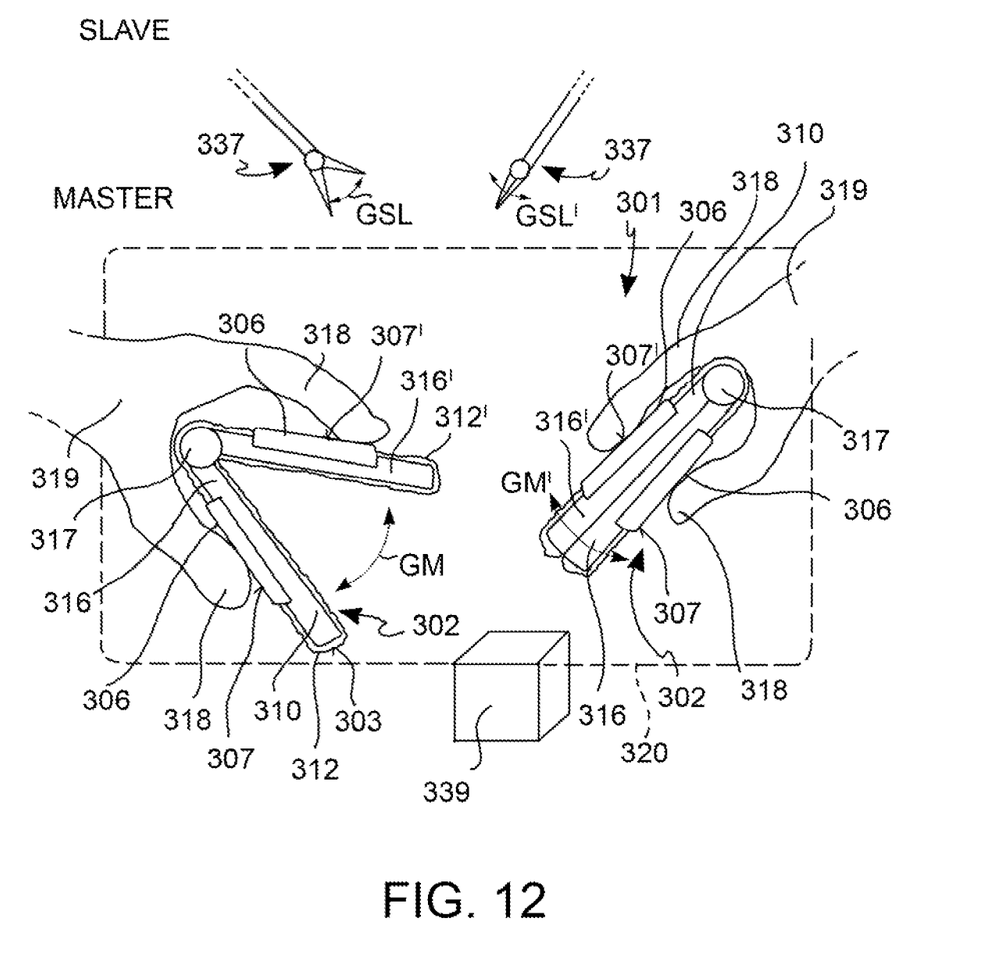
FIG. 12 shows a portion of a master-slave robotic surgery system comprising two sterile master input handle assemblies while hand-held by a surgeon within a work volume and two slave surgical instruments, according to an embodiment.

According to an embodiment, said sterile accessory 306 is integral with said surgical drape 303 as shown for example in FIG. 11, and preferably said sterile accessory 306 is integral with the outer surface 305 of the surgical drape 303. For example, said sterile accessory 306 is welded or glued to said outer surface 305 of the surgical drape 303.

The connector 308 may be integral with the sterile drape 303 and at the same time detachably engaged with the manipulandum 310, while preserving the integrity of the sterile drape 303.

According to a preferred embodiment, the mechanical engagement between said at least one sterile accessory 306 and said non-sterile manipulandum 310 across said sterile surgical drape 303 locks the position and spatial orientation of said manipulandum 310 relative to said interface surface 307 of the accessory 306 in a predefined configuration. Preferably, said locking of position and spatial orientation is achieved while preserving the integrity of the sterile drape 303, and in particular the integrity of the at least one portion of the drape 303 that is covered by said at least one sterile accessory 306.

According to a preferred embodiment, said at least one sterile accessory 306 mechanically engages with said non-sterile manipulandum 310 across said sterile surgical drape 303 in a detachable manner. Thereby, is made possible to re-use the non-sterile manipulandum 310 for several surgeries by sterilization or disposal of the sterile accessory 306 and of the sterile drape 303.

According to an embodiment, said non-sterile manipulandum 310 comprises at least one convex body 309 and said at least one connector 308 of said at least one sterile accessory 306 mechanically engages with said at least one convex body 309.

According to a preferred embodiment, said at least one accessory 306 snap-fits with said non-sterile manipulandum 310, across said sterile surgical drape 303.

Figure 1:
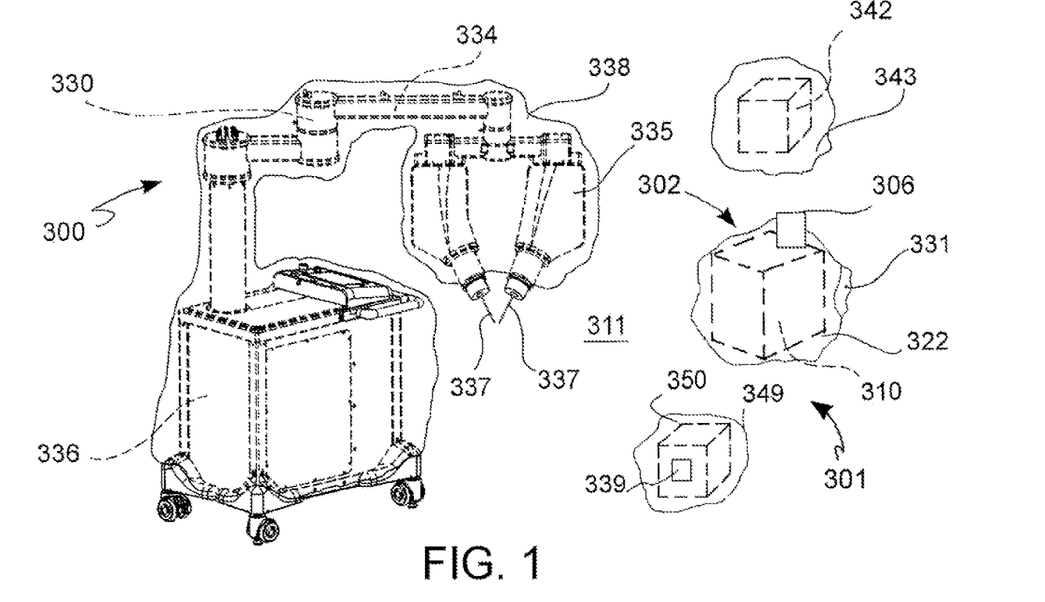
FIG. 1 is an axonometric view that diagrammatically shows a robotic surgery system suitable for microsurgery, according to an embodiment.
Figure 2:
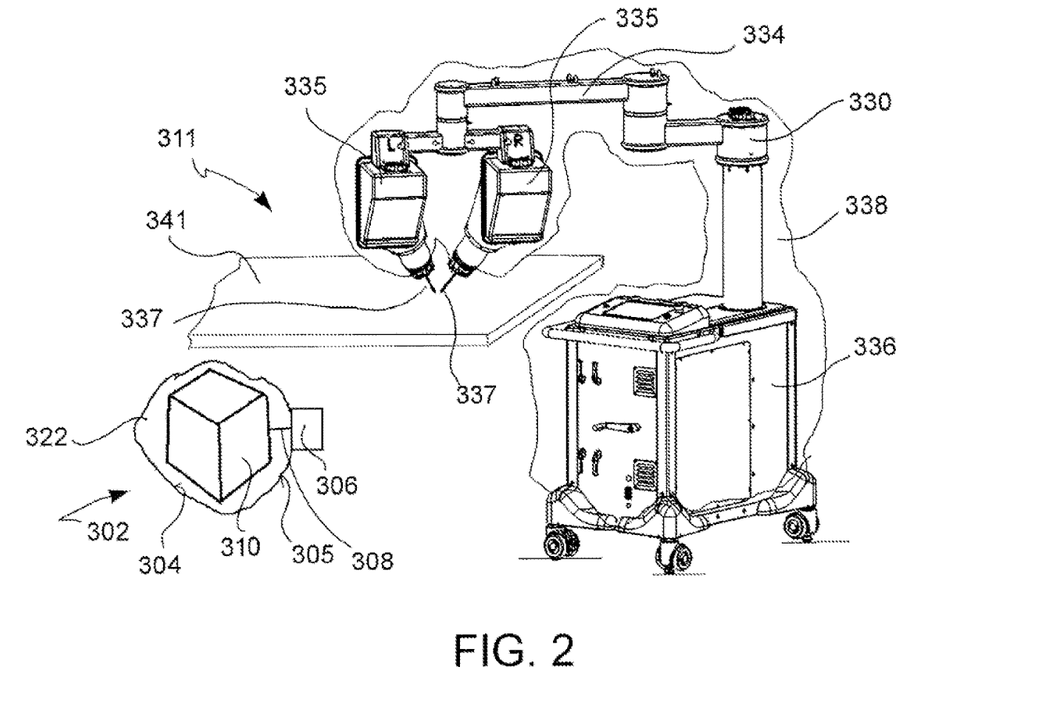
FIG. 2 is an axonometric view that diagrammatically shows a sterile master input handle assembly within a sterile operatory field, according to an embodiment.
Figure 3:
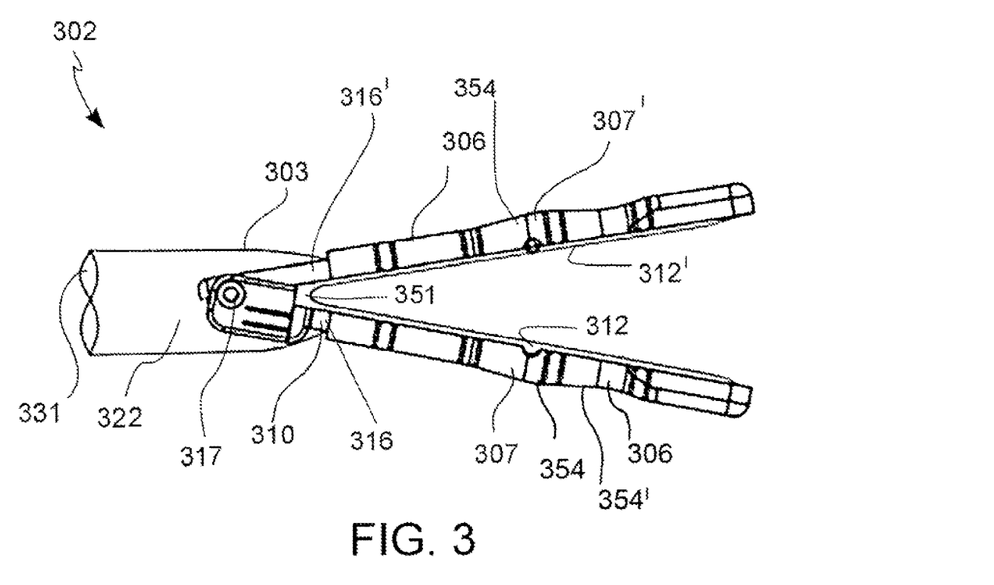
FIG. 3 shows in an elevation view a sterile master input handle assembly, according to an embodiment.
Figure 4:
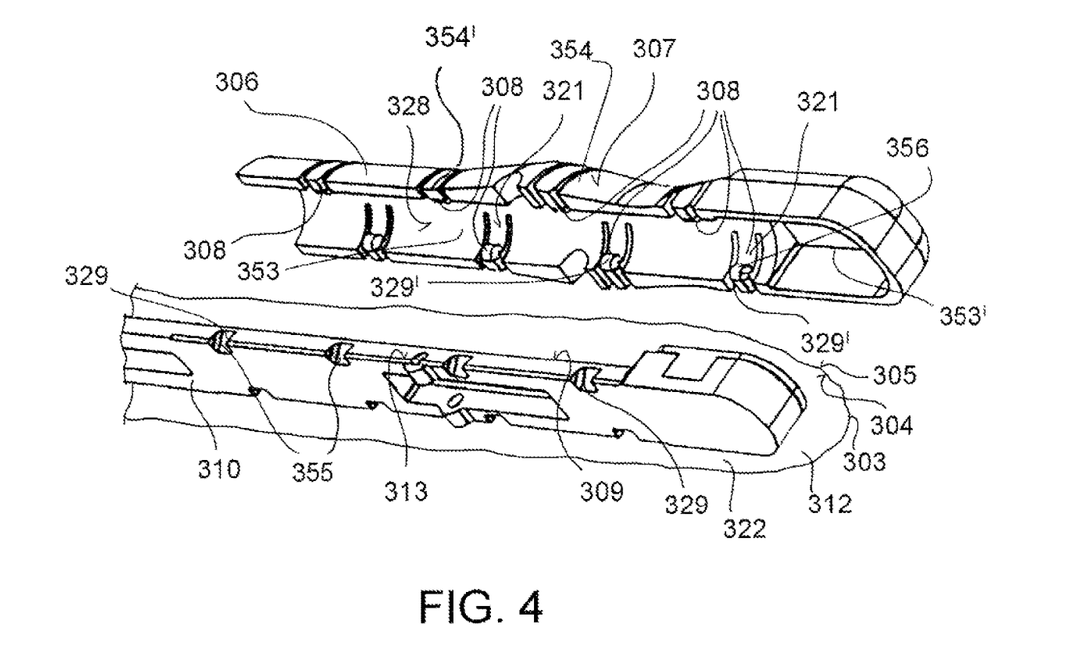
FIG. 4 is an axonometric view showing a portion of a sterile master input handle assembly comprising a draped non-sterile manipulandum and a sterile accessory shown as separated parts, according to an embodiment.
Figure 5:
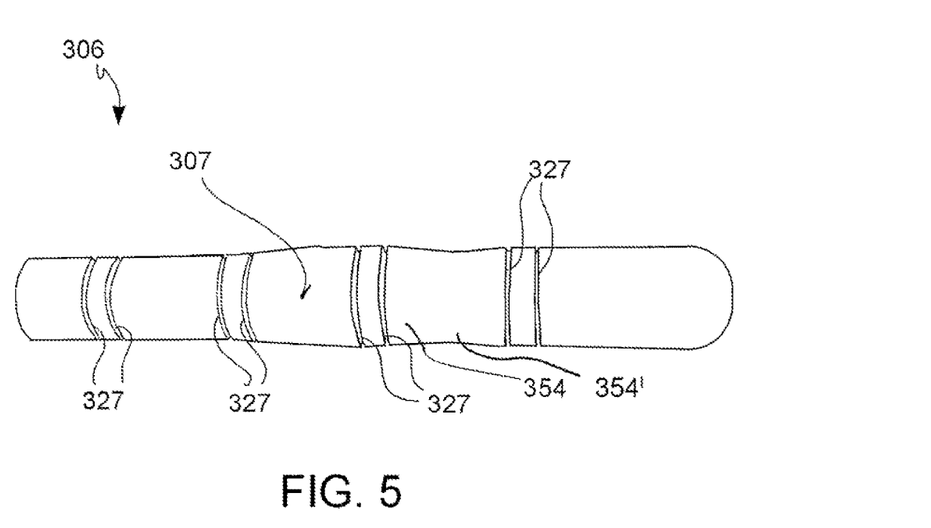
FIG. 5 shows a plan view of an accessory, according to an embodiment.
Figure 6:
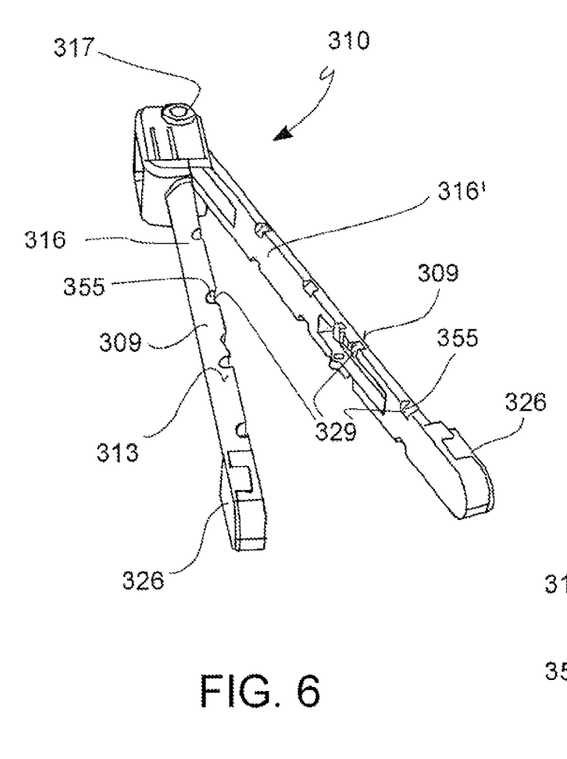
FIG. 6 shows a non-sterile manipulandum in axonometric view, according to an embodiment.

According to a preferred embodiment, said connector 308 of said at least one accessory 306 comprises at least one positioning clip, for snap-fit engaging with at least one undercut wall 329 provided on the body of the non-sterile manipulandum 310. As shown for example in FIG. 4, a sterile accessory 306 comprises a plurality of connectors 308 in form of positioning clips 308 each having a retaining element 329' protruding at or near a free end thereof designed to interlock with a plurality of undercut walls 329 that are provided on respective niches 355 of said non-sterile manipulandum 310. Thanks to the provision of said niches 355 it is possible to avoid relative slip between said sterile accessory 306 and said non-sterile manipulandum 310 across said sterile drape 303. According to an embodiment, the cooperation among said retaining elements 329' of the connector 308 of the sterile accessory 306, said undercut walls 329 and said niches 355 of the non-sterile manipulandum 310 generates an interlocking arrangement that may avoid relative movement, for example relative longitudinal sliding, between said non-sterile manipulandum 310 and said interface surface 307 of said sterile accessory 306.

Cuts 327 may be provided on the accessory 306 to tune the elastic properties of such positioning clips of said connector 308 of the sterile accessory 306. The sterile accessory 306, and particularly the at least one interface surface 307 may be made of rubbery material, in order to favor the grip of the surgeon's fingers thereon. Preferably, in order to mechanically engages the sterile accessory 306 with said non-sterile manipulandum 310, the sterile accessory 306 is placed over a portion of the outer surface 305 of the sterile drape 303 draping the non-sterile manipulandum 310 and then a pressure is applied to the interface surface 307 of the sterile accessory 306 to press the connector 308 with the aim to snap-fit at least one positioning clip of the sterile accessory 306 to at least one respective undercut wall 329 of the non-sterile manipulandum 310. In order to facilitate such mechanical engagement, at least one invitation wall 356 may be provided on or near a portion of said connector 308 of the sterile accessory 306 that is designed to mechanically engage with said non-sterile manipulandum 310 across said sterile drape 303. Preferably, in order not to tear the sterile drape 303, said at least one invitation wall 356 may have a substantially rounded surface, preferably devoid of cut edges that when in contact with the outer surface 305 of the sterile drape 303 may tear the sterile drape 303.

According to an embodiment, said plurality of positioning clips of said at least one connector 308 are suitable to snap-fit engaging with said at least one convex body 309 of the non-sterile manipulandum 310, preferably forming a reversible snap-fit engagement. Preferably, said at least one connector 308, for example comprising a plurality of positioning clips, has an arched concave surface 321 facing said outer surface 305 of the surgical drape 303 so to be suitable for fitting said convex body 309 of the non-sterile manipulandum 310 across the sterile drape 303. For example, the arched concave surface 321 of said at least one connector 308 of the sterile accessory 306 describes substantially the profile of a "C". The sterile accessory 306 itself may comprise an arched concave surface 321 to conform with the shape of said convex body 309 of the non-sterile manipulandum 310, trapping in between a portion of said sterile drape 303.

The at least one sterile accessory 306 may be in the form of a bell or a cap surrounding said sterile drape 303.

The mechanical engagement between said at least one sterile accessory 306 and said non-sterile manipulandum 310 across the sterile drape 303 may be other than a snap-fit engagement. According to an embodiment, the connector 308 of the at least one sterile accessory 306 has at least one male element that mechanically engages with at least one respective female element of the non-sterile manipulandum 310 across the sterile drape 303. According to an embodiment, the at least one sterile accessory 306 and the non-sterile manipulandum 310 are mechanically engaged across the sterile drape 303 by means of a force-fit or interference fit engagement. According to an embodiment, the at least one sterile accessory 306 and the non-sterile manipulandum 310 are mechanically engaged across the sterile drape 303 by means of a screwed or nailed connection.

According to an embodiment, said at least one sterile accessory 306 comprises a second surface 328, or inner surface 328, facing the outer surface 305 of the surgical drape 303. According to an embodiment, said second surface 328 is opposite to said at least one interface surface 307 in respect of the body of said accessory 306, as shown for example in FIG. 4. The second surface 328 is preferably concave in shape forming a concave seat 353 or cavity 353 for receiving the convex body 308, or at least a portion thereof, and a portion of the surgical drape 303 secured, for example pinched or trapped, in between.

According to an embodiment, said at least one interface surface 307 of said at least one sterile accessory 306 has a convex shape. The convexity of the at least one convex interface surface 307 may be realized in a direction transverse to the direction of main longitudinal development of the interface surface 307, to facilitate a rolling movement of the sterile input handle assembly 302 between/among the surgeon's finger of a single surgeon's hand during robotic surgery.

According to an embodiment, said at least one accessory 306 has an elongated shape in a longitudinal direction that substantially fits the convex body 309 and has a convex shape in a direction transverse to said longitudinal direction. According to an embodiment, said at least one interface surface 307 of said at least one accessory 306 has the shape of a bulge, exposing a substantially spherical cap surface to the surgeon's fingers.

According to an embodiment, said at least one convex body 309 of the non-sterile manipulandum comprises at least one convex surface 313, so that said arched concave surface 321 of the accessory 306 substantially conform with said convex surface 313, trapping in between a layer of said sterile drape 303. According to an embodiment, the body of the sterile drape 303 is interposed between, preferably in contact with both, said arched surface 321 of the clip 308 of the accessory 306 and said convex surface 313 of the convex body 309 of the non-sterile manipulandum 310.

According to a preferred embodiment, said sterile master input handle assembly 302 comprises a further or second sterile accessory 306 so as to have at least two sterile accessories 306 (i.e. a first sterile accessory and a second sterile accessory), wherein said at least two sterile accessories 306 cooperate with said non-sterile manipulandum 310 to provide two or more opposite interface surfaces 307 for the surgeon's fingers to grasp and firmly hold said non-sterile manipulandum 310 across said sterile surgical drape 303 in one surgeon's hand. Preferably, said opposite interface surfaces 307 are provided at opposite sides of the non-sterile manipulandum 310 resulting opposite one another in respect of the body of the non-sterile manipulandum 310. Thereby, when the at least two opposite sterile accessories 306 cover at least two opposite portions of the non-sterile manipulandum 310 that have or form cooperating together a grip controller, designed for controlling a paired slave grip degree of freedom of a robotically actuated slave surgical instrument 337 operatively connected to said sterile master input handle 302, the actuation of the grip degree of freedom of the robotically actuated slave surgical instrument 337 is made further intuitive for the surgeon.

According to an embodiment, the sterile drape 303 includes at least one pouch 312, 312' receiving at least a portion of said manipulandum 310 of said master input handle assembly 302. The at least one pouch 312, 312' is at least one portion of said cavity 322 delimited by at least one sleeve 323, 323' of the surgical drape 303 and having a closed end 352.

Figure 7:
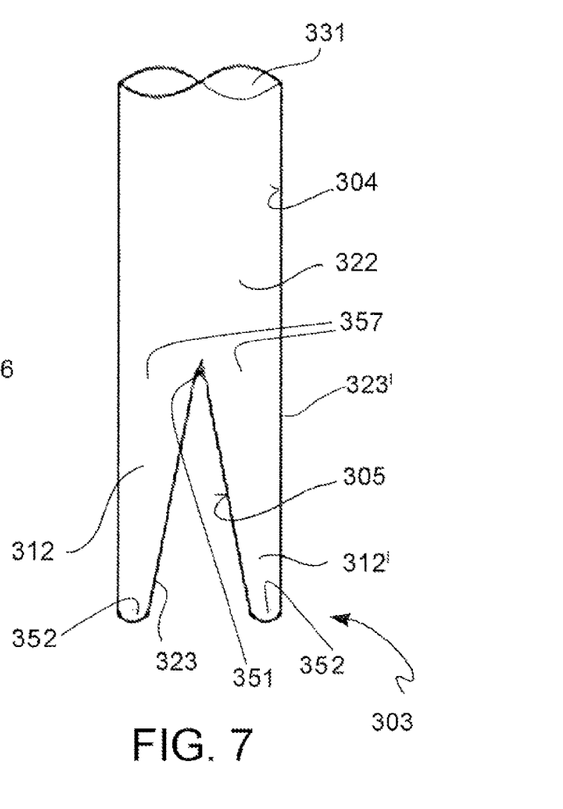
FIG. 7 shows a surgical drape, according to an embodiment.

According to an embodiment non necessarily to be combined with any of the above-mentioned embodiments and as shown for example in FIG. 7, the sterile drape 303 comprises a pair of pouches 312, 312' each receiving at least a portion of a non-sterile manipulandum 310. Thereby, each pouch 312 or 312' of said pair of pouches 312 and 312' receive a portion of said non-sterile manipulandum 310, and said pouches 312, 312' are in mutual fluidic communication. In other words, the body of a single surgical drape 303 delimits a cavity 322 having two pouches 312, 312', preferably the pouches 321, 321' are delimited by means of a pair of sleeves 323, 323' each connected to a respective closed end 352. A drape junction 351 may be formed in the surgical drape 303 at or near a pouch opening 357 of each pouch 312, 312'.

Figure 8:
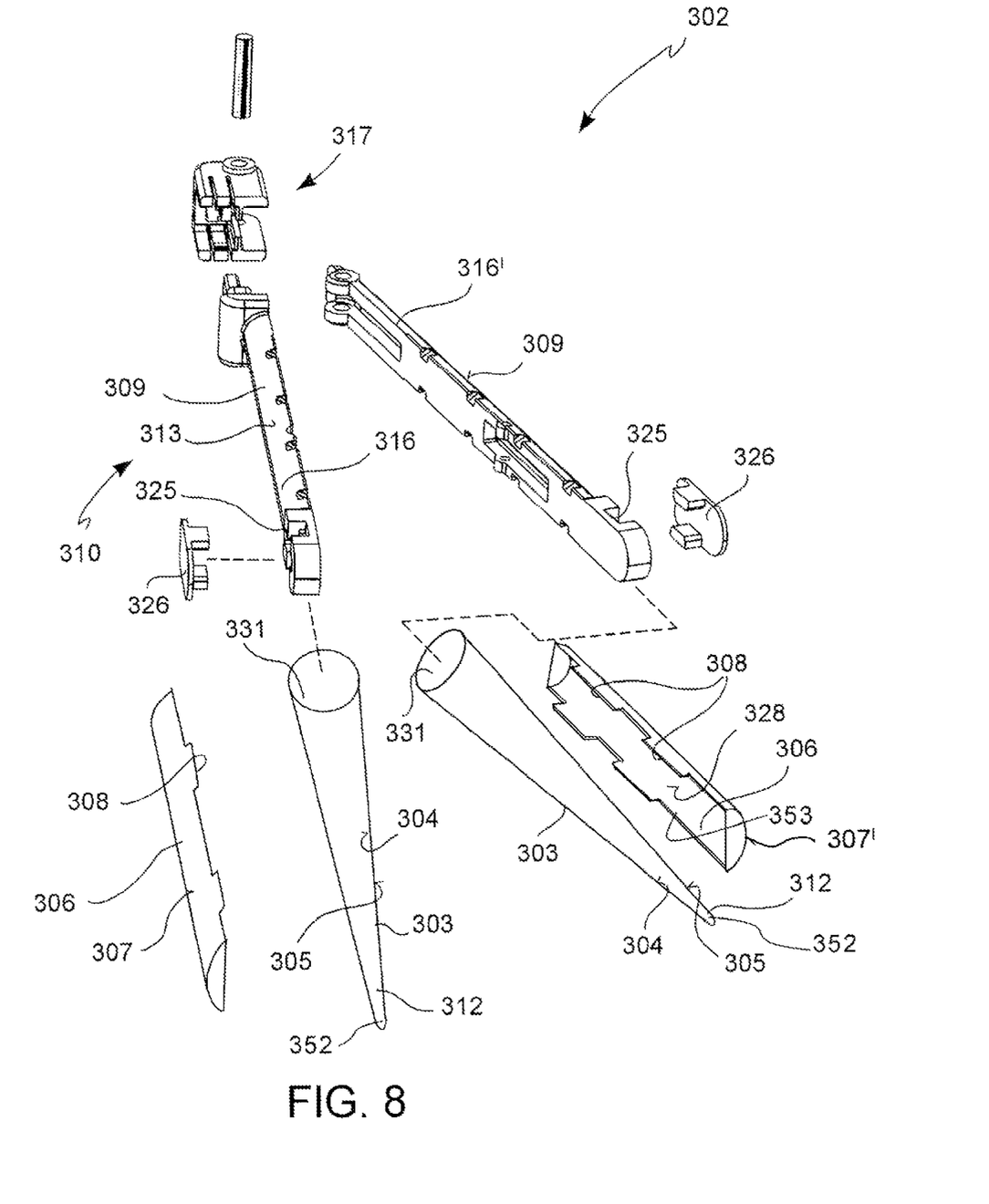
FIG. 8 is an axonometric view that shows a sterile master input handle assembly as separate parts, according to an embodiment.
Figure 9:
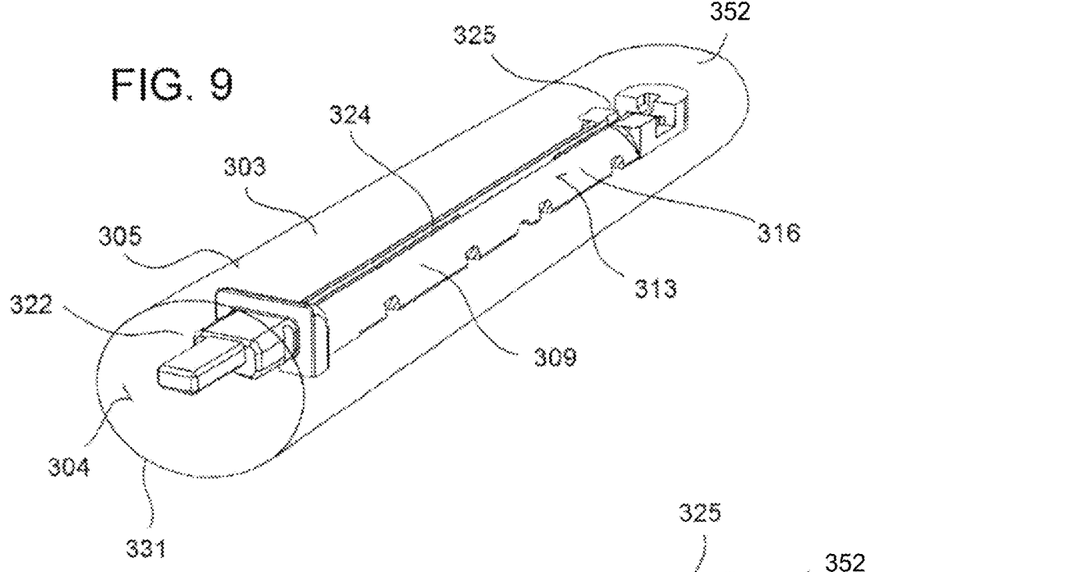
FIGS. 9 and 10 are axonometric views each showing one of the elongated elements of a non-sterile manipulandum in a respective sterile drape pouch, according to an embodiment.
Figure 10:
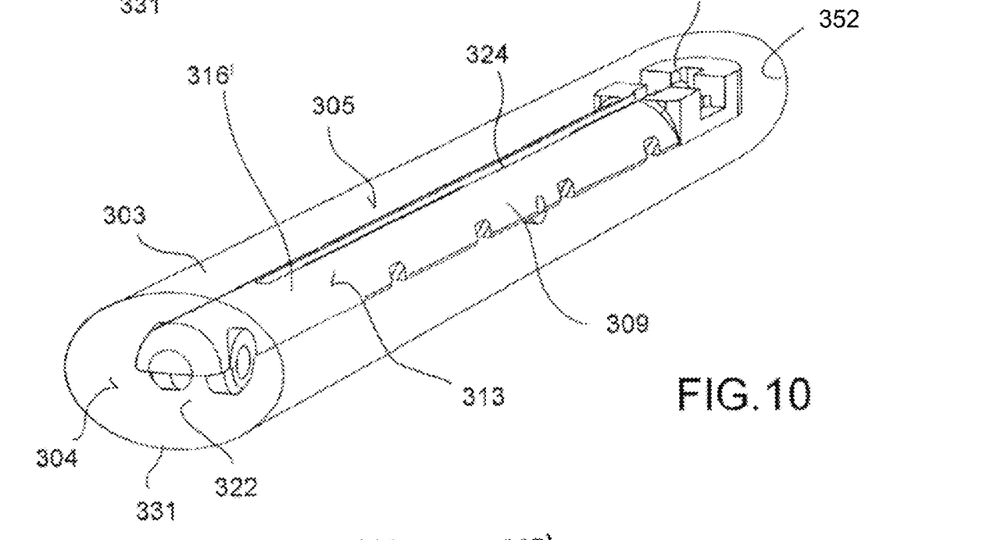

According to another embodiment as shown for example in FIG. 8, the sterile drape 303 comprises two pouches 312, 312' that are made as separate pieces so that the sterile drape 303 comprises multiple drape pieces, each one of the pouches 312, 312' being delimited by a sleeve 323, 323' having a closed end 352 and an opposite pouch opening 357 that may coincide with the drape opening 331 of the respective single drape piece.

According to an embodiment, said at least one sterile accessory 306 is in form of a cheek surrounding at least partially at least one convex body 309 of the non-sterile manipulandum 310, across the sterile drape 303, with the purpose of making the non-sterile manipulandum 310 safer to manipulate when draped by a surgical drape 303. According to an embodiment, said at least one sterile accessory 306 in form of a cheek defines a concave seat 353 facing the outer surface 305 of the sterile drape 303 and preferably in contact with it, the concave seat 353 is designed for hosting a portion of the manipulandum 310.

According to an embodiment, the sterile master input handle assembly 302 comprises at least one degree of freedom between said two opposite interface surfaces 307, 307'. The at least one degree of freedom may be a grip GM, GM' degree of freedom designed to control a paired slave degree of freedom of grip GSL, GSL' of a slave surgical instrument 337, 337'. To activate the grip degree of freedom, the two opposite interface surfaces 307, 307' may be moved, for example moved by means of application of a pressing action, towards each other by the surgeon's fingers 318. Said degree of freedom between the two opposite interface surfaces 307, 307' may be defined by the non-sterile manipulandum 310, which for example comprises two parts 316, 316' movable one in respect to the other, such as two articulated parts and/or a press-button and/or two parts slidingly associated to each other.

Figure 14:
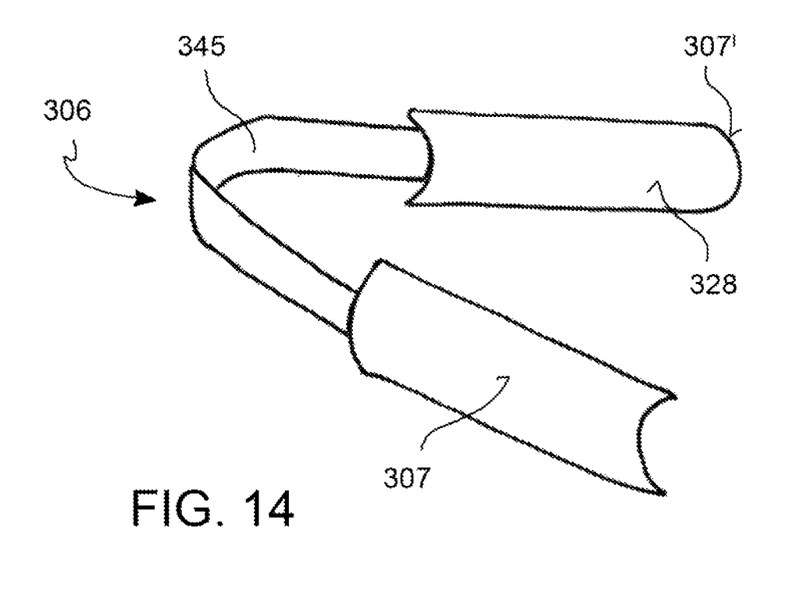
FIG. 14 shows in axonometric view an accessory of a sterile master input handle assembly, according to an embodiment.

According to an embodiment, said degree of freedom between the two opposite interface surfaces 307, 307' is defined by the at least one accessory 306 itself, for example by means of a deformable bridge 345 between two opposite interface surfaces 307, 307' of the accessory 306, as shown for example in FIG. 14. Said degree of freedom between the two opposite interface surfaces may be an elastically loaded degree of freedom. For example, the deformable bridge 345 between two accessories is an elastically deformable bridge, which for example comprises or is made of a flat spring.

According to an embodiment, the elastic action of said elasically-loaded degree of freedom biases said two opposite interface surfaces 307, 307' away to each other.

Figure 13:
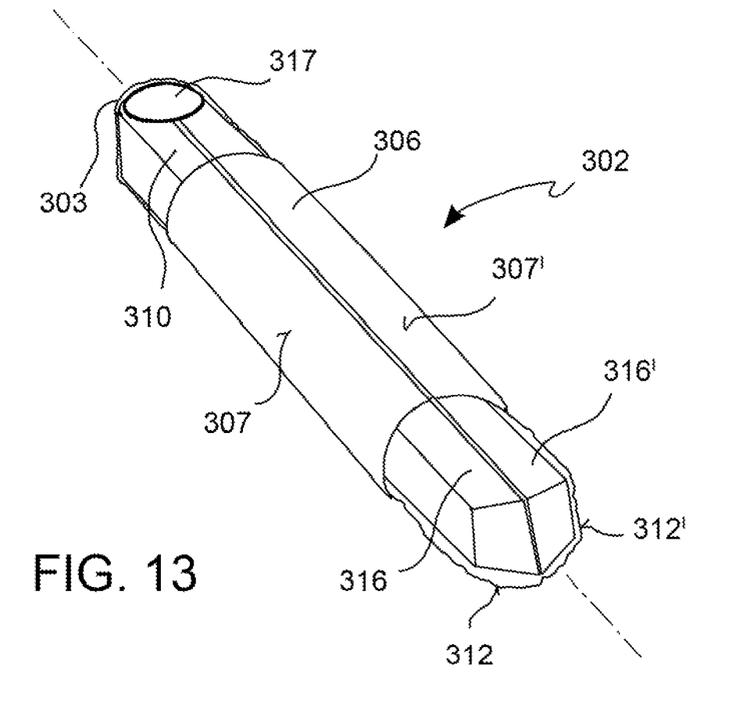
FIG. 13 shows a sterile master input handle in a configuration wherein the interface surfaces draw together a cylindrical convex geometry, according to an embodiment.

In at least one configuration said two opposite interface surfaces 307, 307' define together a convex, cylindrical geometry, as shown for example in FIG. 13. For example, when the sterile master input handle assembly 302 is in a closed configuration, the closed configuration might be obtained by moving towards each other two articulated parts of the non-sterile manipulandum 310 and/or the two opposite interface surfaces 307, 307', then the two opposite interface surfaces define together a convex, cylindrical geometry. The provision of such a convex, cylindrical geometry favors the rolling of the sterile master input handle assembly between/among the surgeon's fingers 318 of a surgeon's hand 319. Said two opposite sterile accessories may be made in single piece, in other words said two sterile accessories may be monobloc.

According to a preferred embodiment, said non-sterile manipulandum 310 comprises at least a pair of elongated elements 316, 316' hinged one another forming a tool joint 317, for example a pin joint 317. Preferably, said elongated elements 316, 316' are rigid bodies. According to a preferred embodiment, the terminology "rigid body" means that such a body is deficient or devoid of flexibility. According to an embodiment, the terminology "rigid body" means that such a body is unable to provide elastically flexural deformation when in operative conditions. According to an embodiment, the sterile drape 303 is made of material that allows relative movement between the elongated elements 316, 316' of the manipulandum 310. Thereby, the sterile drape 303 is flexible or at least partially flexible so that it allows the spatial movement of the manipulandum 310 and allows to move each and all the degrees of freedom of the manipulandum, such as a gripping degree of freedom thereof.

Thereby, as the sterile drape 303 comprises a pair of pouches 312, 312' in single or multiple pieces, it is possible to individually house the elongated elements 316, 316' of said pair of said elongated elements 316 or 316' within a respective pouch 312 or 312'.

According to an embodiment, the sterile drape 303 comprises a bifurcation from which said pair of pouches 312, 312' extend distally.

According to an embodiment, at least one of the elongated elements 316, 316' of said non-sterile manipulandum 310, and preferably each of said elongated elements 316, 316', comprises at least one convex body 309. Thereby, said at least one convex body 309 is a portion of at least one elongated element 316, 316' of said master input tool 310.

According to an embodiment, said at least one elongated element 316, 316' and preferably each of said elongated elements 316, 316', comprises a groove 324, preferably located along the at least one convex body 309 thereof, designed to receive at least a portion of the yielding body of the surgical drape 303 when the sterile accessory 306 is mechanically engaged with a portion of the non-sterile manipulandum 310. For example, wrinkles and the like of the surgical drape 303 may find room within said groove 324 of the non-sterile manipulandum 310 to favor the mechanical engagement of the sterile accessory 306 to the non-sterile manipulandum 310.

According to an embodiment, said at least one elongated element 316, 316' and preferably each of said elongated elements 316, 316', delimits a sensor slot 325 for housing at least a portion of a sensor, preferably in a detachable manner. The slot 325 may comprise abutment reference surfaces for the sensor with the purpose of receiving the sensor in a predefined accurate position and/or orientation with respect to the body of the elongated element 316, 316'. For example, said sensor is a tracking sensor suitable to cooperate with a tracking fieldfield generator 339 provided within the sterile operatory field 311 for example near or at a master console 350.

The master console 350 may comprise at least one tracking field generator that may be provided integral with the surgeon, for example the tracking field generator is on a wearable item to be worn by the surgeon such as a belt or bracelet or the like, or the at least one tracking field generator may be provided on a surgical chair or the at least one tracking field generator may be provided on the master console 350. The console 350 may comprise a tower for the surgeon to stand near to the console 350 and the tracking system 339 may be integral with the tower of the master console 350.

According to an embodiment, said groove 324 of the manipulandum 310 is also suitable to receive a cable connection to said sensor when received within said slot 325. A cover 326 or lid 326 may be provided to cover said slot 325. A sensor slot seat may be provided on the second surface 328 of said sterile accessory 306 of size and shape suited to receive said sensor slot 325 with or without said lid 326, and said sensor slot seat may be in communication with said concave seat 353 and/or a part thereof. The portion of the sterile accessory 306 covering said sensor slot 325 of an elongated element 316, 316' of the non-sterile manipulandum 310 may be devoid of connectors so as to not interfere with the sensor detection of the sensor received in said sensor slot 325. Preferably, said sensor is a magnetic tracking sensor (i.e. a magnetometer) cooperating with said tracking field generator.

According to an embodiment, the tracking system 339 is an optical tracking system comprising at least one camera, for example a set of stereoscopic cameras, and the master input handle assembly 302 comprises at least one optical marker with the purpose of being optically tracked by the tracking system. Said one or more slots 325 and/or said groove 324 may act as optical marker.

According to an embodiment, said at least one accessory 306 is disposable, in other words is designed to have a single-use in a sterile environment.

According to an embodiment, said at least one accessory 306 is designed to be sterilized, so that can be re-utilized for several surgeries.

Thanks to the provision of such an accessory 306 forming an increased friction surface 307 with the purpose to form a surface for the surgeon fingers to handle a non-sterile manipulandum 310, it is avoided the need to dispose the non-sterile manipulandum 310 after a single surgery session. Therefore, the non-sterile manipulandum 310 is maintained sterile by covering it with the sterile drape 303. Moreover, the provision of the accessory 306 makes the surgeon feels to firmly and precisely hold the draped non-sterile manipulandum 310.

Thanks to the provision of such at least one interface surface 307, a surgeon may alternate hand microsurgery and robotic-aided microsurgery during a single intervention, without for this reason compromise the sterility of the sterile operatory field 311. Thereby, it is avoided the need of dispose the non-sterile manipulandum 310 each time the surgeon switches from hand microsurgery to robotic-aided microsurgery and vice-versa during a single intervention.

According to a general embodiment, it is provided a master controller assembly 301 for robotic surgery comprising at least one sterile master input handle assembly 302 according to any one of the embodiments described above and a master console 350. The master controller assembly 301 is designed to control a slave robot assembly 330.

The master controller assembly 301 may be remotely located, and the master console 350 may be remotely located.

The master controller assembly 301 may be draped and located within a sterile operatory field 311, and at this end the master console 350 of the master controller assembly 301 may be draped by a console drape 349.

According to an embodiment, the master controller assembly 301 comprises a tracking system 339, which may belong to the master console 350, such as an optical and/or magnetic tracking system suitable to track position and/or orientation of at least one portion of the sterile master input handle assembly 302, and/or of the non-sterile manipulandum 310 within a predefined tracking volume.

The master input handle assembly 302 may be mechanically ungrounded and mechanically unconstrained with respect to the tracking system 339 of the master console 350 and/or with respect to the master console 350, and designed to be hand-held by the surgeon.

According to an embodiment, a pair of mechanically ungrounded, mechanically unconstrained sterile master input handle assemblies 302 are provided, each designed to be hand-held by a single hand of the surgeon, so that the surgeon holds during robotic surgery two master input handles 302, one in each surgeon's hand. The two mechanically ungrounded, mechanically unconstrained sterile master input handle assemblies 302 may control, for example individually, two paired slave surgical instruments 337 of the robotic surgery system 300.

According to a general embodiment, it is provided a robotic surgery system 300 suitable for microsurgery comprising at least one sterile master input handle assembly 302 according to any one of the embodiments described above.

Preferably, said robotic surgery system 300 comprises at least one master console 350.

According to a preferred embodiment, said robotic surgery system 300 further comprises a slave robot assembly 330. According to an embodiment, said slave robot assembly 330 comprises at least one surgical arm 334 manipulating said surgical instrument 337. According to an embodiment, said salve robot assembly 330 comprises at least one micromanipulator 335 manipulating said surgical instrument 337. Preferably, said at least one micromanipulator 335 is directly connected in series to said surgical arm 334 forming a kinematic chain with said surgical arm 334 and manipulates said surgical instrument 337. According to an embodiment, at least two micromanipulators 335 are directly connected in series to said surgical arm 334 forming an at least two-branched kinematic chain with said surgical arm 334. According to an embodiment, said slave robot assembly 330 comprises at least one robotic cart 336 and said at least one arm 334 extends from the robotic cart 336.

According to an embodiment, said robotic surgery system 300 comprises a control unit, the tracking system 339 may belong to the control unit, the control unit being suitable for receiving at least a position and orientation associated to said non-sterile manipulandum 310 and suitable for transmitting a command signal to the slave robot assembly 330 to actuate said surgical instrument 337. According to an embodiment, said control unit is suitable for receiving a first command signal containing information about said manual command and to transmit a second command signal containing information about said manual command to the slave robot assembly 330 in order to actuate said surgical instrument 337.

The control unit preferably belongs to the master console 350.

According to an embodiment, said robotic surgery system 300, and preferably said master console 350 of said robotic surgery system 300, further comprises at least one tracking system 339 comprising a field generator, suitable to detect within a predefined tracking volume position and orientation of said non-sterile manipulandum 310, preferably through detection of the at least the position of the sensors housed within said slots 325 and/or the position of said slots 325.

According to an embodiment, said at least one tracking system 339 generates said predefined tracking volume, for example by means of a field generator, for example a magnetic field generator and/or an optical camera set. For example, said magnetic field generator is located integral with the surgeon.

At least one slave drape 338 may be provided to drape at least a portion of the robotic slave assembly 330.

Preferably, said master manipulator 310 and/or said sterile master input handle 302 controls the slave robotic surgery system 300 activating at least a grip degree of freedom of an articulated end-effector located at or near the distal end of the shaft of the surgical instrument 337.

The sterile master input handle 302 preferably also controls the positioning of the slave robot assembly 330 by means of controlling said at least one micromanipulator 335, which for example is a Carthesian manipulator having three orthogonal linear degrees of freedom. The manipulator 335 is preferably upstream the shaft of the surgical instrument 337. The articulated end effector located at or near the distal end of the shaft of the surgical instrument 337 may comprise also a pitch and a yaw degrees of freedom, which can be controlled by said sterile master input handle assembly 302. The articulated end effector of the surgical instrument 337 preferably comprise pitch, yaw and grip degrees of freedom, and the surgical instrument 337 may also comprise a roll degree of freedom about the shaft thereof.

According to an embodiment, said robotic surgery system 300 further comprises at least one surgical microscope 342. A microscope drape 343 may be provided for draping at least a portion of the microscope 342.

According to a general embodiment, it is provided a sterile operatory field 311 comprising at least one sterile master input handle assembly 302 according to any one of the embodiments described above.

According to an embodiment, said sterile operatory field 311 further comprises at least a portion of at least one robotic slave manipulator 330 according to any one of the embodiments described above. Thereby, said sterile operatory field 311 further comprises at least a portion of at least one robotic surgery system 300 according to any one of the embodiments described above.

According to an embodiment, said sterile operatory field 311 further comprises at least one operatory bed 341 providing a support for a patient's anatomy to be treated.

According to a general embodiment, it is provided a surgical drape 303 for a master input handle assembly 302 comprising in single piece a pair of pouches 312, 312' for individually receiving a pair of elongated elements 316, 316' of a non-sterile manipulandum 310. The surgical drape 303 may be associated to one or more sterile accessories 306 according to any one of the embodiments described above. The non-sterile manipulandum 310 of the surgical drape 303 may be a non-sterile manipulandum 310 according to any of the embodiments described above.

Thanks to the features described above, provided either alone or in combination in particular embodiments, it is possible to respond to the above-mentioned needs providing the above-cited advantages, and in particular:

- it is made easier to control a robotic surgery system from a sterile environment, such as a sterile operatory field;
- it is provided a sterile master controller comprising a non-sterile manipulandum suited to receive a manual command from the surgeon across and through a drape sheet having at least one accessory that allows the non-sterile manipulandum 310 to be confidently grasped by the surgeon across the sterile barrier;
- it is avoided the contamination of the non-sterile manipulandum 310 that may comprise the most expensive features such as sensors, reference surfaces, optical markers, rotational joints, and the like, which therefore can be used for several surgeries;
- thanks to the provision of said assembly having a drape 303 draping a non-sterile manipulandum 310 it is allowed to locate the sterile master handle assembly 302, and therefore the surgeon, within the sterile operatory field 311, for example near the operatory bed 341;
- thereby, it is allowed the surgeon to alternate hand microsurgery and robotic-aided microsurgery during a single intervention, without for this reason needing to sterilize the master controller;
- the draped unconstrained master manipulandum may in its entirety be moved freely within a master work volume near the operatory bed avoiding contamination of the master manipulandum;
- thanks to the provision of such a sterile accessory, it is provided a solution able to drape a master controller preserving sterility and at the same time making the master input tool easier to manipulate when draped by a surgical drape;
- at the same time, thanks to the connector 308 of the accessory 306 the sterile drape 303 results easier to fit around the non-sterile manipulandum 310;
- no need to make a master controller disposable is envisaged even in case of handling the master input tool within a sterile operatory field, as the master input tool can be draped without for this reason loosing grip for the surgeon;
- the master sterile drape 303 may have a loose body that drapes air other than the non-sterile manipulandum 310, therefore thanks to the provision of said at least one connector 308 it is allowed to constrain a portion of the drape 303 to a portion of the non-sterile manipulandum 310, preferably at or near the at least one convex body 309 thereof;
- thereby, the connector 308 at the same time locally close-fits the body of the sterile drape 303 against non-sterile manipulandum 310 and holds the friction surface 307 in place.

To the embodiments described above, one skilled in the art may, to satisfy contingent and specific needs, make numerous modifications, adaptations, and replacements of elements with others that are functionally equivalent, without however departing from the scope of the appended claims.

LIST OF REFERENCES

300 Robotic surgery system, or robotic microsurgery system
301 Master workstation of the robotic surgery system
302 Master sterile handle assembly
303 Surgical drape, or sterile drape, or drape
304 Inner non-sterile surface of the sterile drape
305 Outer sterile surface of the sterile drape
306 Sterile accessory, or accessory
307 Interface surface, or surface, of the sterile accessory
308 Connector of the sterile accessory
309 Convex body of the manipulandum
310 Non-sterile manipulandum of the master sterile handle assembly
311 Sterile operatory field
312, 312' Pouch of the sterile drape
313 Convex surface of the convex body
316, 316' Elongated element of the manipulandum
317 Joint
318 Surgeon's finger
319 Surgeon's hand
320 Work volume
321 Arched clip surface
322 Drape cavity
323, 323' Drape sleeve
325 Sensor slot
326 Cover or lid
327 Cuts, or notches
328 Second surface of the accessory
329 Undercut walls
329' Retaining elements
330 Slave robotic assembly
331 Opening of the drape
334 Robotic arm
335 Manipulators 336 Robotic cart
337 Surgical instrument
338 Slave drape
339 Tracking system
341 Operatory bed
342 Surgical microscope
343 Microscope drape
345 Bridge
349 Master console drape
350 Master console
351 Junction of the sterile drape
352 Closed end of the sterile drape
353 Concave seat of the accessory
353' Seat or cavity for the sensor slot
354 Bump of the accessory
354' Recess of the accessory
355 Niche
356 Invitation wall
357 Pouch opening

The invention claimed is:

1. A sterile master input handle assembly comprising:
a non-sterile manipulandum; and
a sterile surgical drape draping said non-sterile manipulandum;
wherein:
said sterile master input handle assembly is mechanically ungrounded and comprises features designed to be tracked by a tracking system to determine position and/or orientation of the master input handle assembly within a predefined work volume for controlling at least one paired slave surgical instrument;
said sterile master input handle assembly further comprises at least one sterile accessory, suitable to form a sterile interface of the sterile master input handle assembly for the surgeon's fingers;
said at least one sterile accessory mechanically engages with said non-sterile manipulandum across said sterile surgical drape;
said at least one sterile accessory covers at least one portion of the outer surface of the surgical drape;
said at least one sterile accessory includes at least one interface surface forming said sterile interface for the surgeon's fingers to manipulate the non-sterile manipulandum across said sterile surgical drape, wherein said interface surface is a convex friction surface having a predefined value of surface roughness greater than the surface roughness of the outer surface of said sterile surgical drape;
said at least one sterile accessory forming a sterile handgrip;
said sterile master input handle assembly comprises a further, second sterile accessory so as to have at least two sterile accessories, said one sterile accessory and said further, second sterile accessory provide two opposite interface surfaces for the surgeon's fingers to grasp said non-sterile manipulandum across said sterile surgical drape;
said sterile master input handle assembly comprises a degree of freedom between said two opposite interface surfaces.

2. The sterile master input handle assembly according to claim 1, wherein said two sterile accessories are provided at opposite sides of the non-sterile manipulandum.

3. The sterile master input handle assembly according to claim 1, wherein said degree of freedom is an elastically loaded degree of freedom.

4. The sterile master input handle assembly according to claim 1, wherein in at least one configuration said two opposite interface surfaces define together a convex, cylindrical geometry.

5. The sterile master input handle assembly according to claim 1, wherein said two sterile accessories are made as a single piece.

6. The sterile master input handle assembly according to claim 1, wherein said non-sterile manipulandum comprises at least a pair of elongated elements hinged one another forming a tool joint; wherein at least one of the elongated elements comprises at least one convex body; and wherein at least one sterile accessory is engaged with the convex body.

7. The sterile master input handle assembly according to claim 6, wherein each of said elongated elements comprises said convex body and each of said sterile accessory is engaged with the convex body of each of said elongated elements.

8. The sterile master input handle assembly according to claim 6, wherein the sterile drape comprises a pair of pouches for respectively receiving at least at least a pair of said elongated elements.

9. The sterile master input handle assembly according to claim 8, wherein the sterile drape comprises a bifurcation from which said pair of pouches extend distally.

10. The sterile master input handle assembly according to claim 1, wherein said at least one interface surface comprises bosses and/or valleys to receive the surgeon's fingers.

11. The sterile master input handle assembly according to claim 1, wherein said at least one sterile accessory snap-fits with said non-sterile manipulandum, across said sterile surgical drape.

12. The sterile master input handle assembly according to claim 1, wherein said at least one sterile accessory mechanically engages with said non-sterile manipulandum across said sterile surgical drape in a detachable manner.

13. The sterile master input handle assembly according to claim 1, wherein said at least one sterile accessory is integral with said surgical drape.

14. Robotic surgery system comprising:
at least one sterile master input handle assembly according to claim 1, and
at least one slave robot assembly comprising at least one surgical instrument.

* * * * *